(12) United States Patent
Baba et al.

(10) Patent No.: US 7,777,066 B2
(45) Date of Patent: Aug. 17, 2010

(54) GLYCERO-COMPOUND HAVING TRIPLE BOND AND MEMBRANE MATERIAL CONTAINING THE SAME

(75) Inventors: Teruhiko Baba, Tsukuba (JP);
Toshiyuki Takagi, Ushiku (JP);
Toshiyuki Kanamori, Tsukuba (JP)

(73) Assignee: National Institute of Advanced Industrial Science and Technology (JP)

( * ) Notice: Subject to any disclaimer, the term of this patent is extended or adjusted under 35 U.S.C. 154(b) by 920 days.

(21) Appl. No.: 11/555,857

(22) Filed: Nov. 2, 2006

(65) Prior Publication Data

US 2007/0105823 A1    May 10, 2007

(30) Foreign Application Priority Data

Nov. 7, 2005    (JP)    ............... P2005-322170

(51) Int. Cl.
*C07F 9/02*    (2006.01)
(52) U.S. Cl. ..................................... 558/186
(58) Field of Classification Search .............. None
See application file for complete search history.

(56) References Cited

OTHER PUBLICATIONS

Heinz et al, Chemistry and Physics of Lipids, Synthesis and Enzymic Conversion of an Ether Analog of Monogalactosyl Diacylglycerol, 1979, 24(3), pp. 265-276.*

\* cited by examiner

*Primary Examiner*—Paul A Zucker
(74) *Attorney, Agent, or Firm*—Ostrolenk Faber LLP

(57) ABSTRACT

The present invention provides a chemically stable and novel glycero-compound having one or two triple bonds, one molecule of a glycerol and one or two molecules of a fatty alcohol having a triple bond being linked through an ether bond, an organic group being linked to residual hydroxyl groups of the glycerol, which can be used as a membrane material for forming a vesicle membrane due to its high intermolecular cohesive force, and also provides a membrane forming material containing the same. The glycero-compound has a triple bond represented by the following general formula (1):

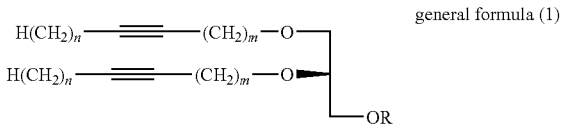

general formula (1)

wherein n and m each represents a number of 1 to 17 and the total (n+m) is a number of 4 to 18, n and m may be the same or different, and R represents a hydrogen atom, a metal atom, a phosphoric acid group, or an organic group which may be linked through a phosphoric acid group.

6 Claims, No Drawings

GLYCERO-COMPOUND HAVING TRIPLE BOND AND MEMBRANE MATERIAL CONTAINING THE SAME

BACKGROUND OF THE INVENTION

1. Field of the Invention

The present invention relates to glycero-compounds having a triple bond and, more particularly, to novel glycero-compounds (lipids) having a triple bond which is useful as organic thin membrane materials capable of serving as a drug carrier by sealing a water soluble drug in an inner water phase of a vesicle or dissolving an oil soluble drug into a vesicle, surface modifiers of various industrial products (fiber, plastic, glass, metal, ceramic, etc.), organic thin membrane materials for modifying the surface of a biopolymer such as membrane protein or nucleic acid, and dispersing agents, emulsifiers, deemulsifiers, detergents, solubilizers, humectants and penetrants of cosmetics, foods and dyes, and to membrane forming materials containing the same Priority is claimed on Japanese Patent Application No. 2005-322170, filed Nov. 7, 2005, the content of which is incorporated herein by reference.

2. Description of Related Art

A glycero-compound (lipid), in which one molecule of a glycerol and one or two molecules of a saturated or unsaturated fatty acid are linked through an ester bond, is widely used as treating agents for various industries used for mining, metal working, surface finishing and cleaning as well as various domestic detergents and cleaners because of its surface activity, and is also widely used as additives for drugs, cosmetics and foods because of its high safety.

A glyceryl ester of a saturated or unsaturated fatty acid of this kind is obtained by partial saponification of naturally produced triglyceride, or by linking one molecule of a glycerol and one or two molecules of a saturated or unsaturated fatty acid through an ester bond. Furthermore, a noncyclic phospholipid, in which residual hydroxyl groups are linked to a phosphoric acid group, is not only naturally produced, but also synthesized by artificial means.

Even if the glyceryl ester of the saturated fatty acid or the phospholipid derived therefrom is hydrated or not, it solidifies with no fluidity or its solid dispersion when a fatty acid chain solidifies with the decrease in temperature. It is known that the temperature at which this change occurs depends on the chain length of the fatty acid, and it solidifies at lower temperature when the chain length increases. In applications such as surface modification treatment, it becomes difficult to handle because of poor fluidity.

It is known that, in the case of the glyceryl ester of the unsaturated fatty acid or the phospholipid derived therefrom, the temperature at which it solidifies is usually lower than that in the case of the saturated fatty acid, and an unsaturated bond is oxidatively decomposed with oxygen in an air, easily. Therefore, it is difficult to apply the glycerol ester of the unsaturated fatty acid or the phospholipid derived therefrom to various uses for comparatively long period.

A lot of fatty acids and glyceryl esters, which have a double bond, exist in the natural world. Also glyceryl esters and glyceryl ethers, which have a double bond introduced therein, have hitherto been synthesized, artificially. There has also been synthesized a lipid in which an unsaturated bond such as diene (two double bonds) or diyne (two triple bonds) is conjugated so as to impart polymerizablity.

On the other hand, extremely little fatty acids having a monoyne (one triple bond) exist in the natural world. For example, fatty acids having a monoyne exist as 9-octadecynoic acid in oil extracted from seeds of plants belonging to the genus *Santalaceae*, as shown in non-patent document 1. However, a complex lipid containing the same such as phospholipid has never been known.

Furthermore, an ester type phospholipid having a monoyne at the end of the hydrophobic chain has been synthesized (Chem. Phys. Lipids, 112, 99-108 (2001)). However, the ester type phospholipid is not suited for use as a membrane base material for reconstituting a membrane protein because of its short chain length (13 carbon atoms) of the hydrophobic group. Also the monoyne at the end is not suited for use as a drug carrier material in the living body in view of biodegradability because of its high polymerizability.

Non-patent document 1: Tetrahedron Lett., No. 40, 3011-3013 (1964))

Non-patent document 2: Chem. Phys. Lipids, 112, 99-108 (2001)

A glyceryl ether derivative, which contains a non-polymerizable triple bond introduced therein and is chemically stable, has never been found.

SUMMARY OF THE INVENTION

An object of the present invention is to provide a chemically stable and novel glycero-compound having one or two triple bonds, one molecule of a glycerol and one or two molecules of a fatty alcohol having a triple bond being linked through an ether bond, an organic group being linked to residual hydroxyl groups of the glycerol. The glycero-compound can be produced in a high purity state within a short period of time and is not converted into a solid or into its solid dispersion within a wide temperature range, and also can be used as a membrane material for forming a vesicle membrane due to its high intermolecular cohesive force, and to provide a membrane forming material containing the same.

The present inventors have intensively studied and found that, when a fatty alcohol derivative having one triple bond is obtained and when the fatty alcohol derivative and a chiral glycerol derivative compound are used, it is possible to produce a group of compounds which can be called chiral compounds and thus the present invention has been completed.

That is, according to this application, the following inventions are provided.

(1) A glycero-compound having a triple bond represented by the following general formula (1):

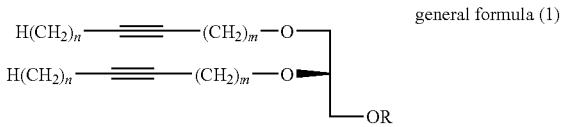

general formula (1)

wherein n and m each represents a number of 1 to 17 and the total (n+m) is a number of 4 to 18, n and m may be the same or different, and R represents a hydrogen atom, a metal atom, a phosphoric acid group, or an organic group which may be linked through a phosphoric acid group.

(2) A glycero-compound having a triple bond represented by the following general formula (2):

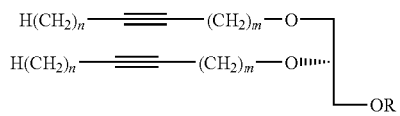

general formula (2)

wherein n, m and R are as defined in the general formula (1).

(3) An isomer mixture containing the compound described in (1) and the compound described in (2).

(4) A glycero-compound having a triple bond represented by the following general formula (3):

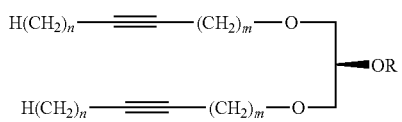

general formula (3)

wherein n, m and R are as defined in the general formula (1).

(5) A glycero-compound having a triple bond represented by the following general formula (4):

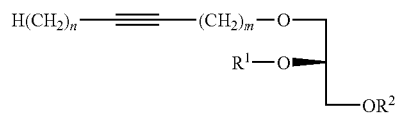

general formula (4)

wherein n and m are as defined in the general formula (1), $R_1$ represents a hydrogen atom, an alkyl group, a cyclic alkyl group, an aryl group or an aralkyl group, and also may have a double bond, and $R_2$ represents a hydrogen atom, a metal atom, or an organic group which may be linked through a phosphoric acid group.

(6) A glycero-compound having a triple bond represented by the following general formula (5):

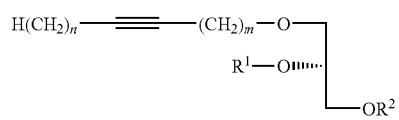

general formula (5)

wherein n, m, $R^1$ and $R^2$ are as defined in the general formula (4).

(7) An isomer mixture containing the compound described in (5) and the compound described in (6).

(8) A glycero-compound having a triple bond represented by the following general formula (6):

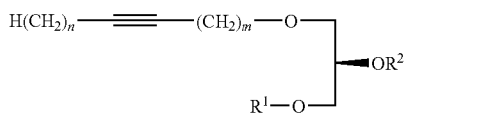

general formula (6)

wherein n, m, $R^1$ and $R^2$ are as defined in the general formula (4).

(9) A glycero-compound having a triple bond represented by the following general formula (7):

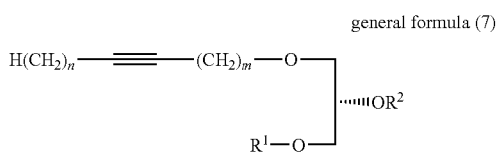

general formula (7)

wherein n, m, $R^1$ and $R^2$ are as defined in the general formula (4).

(10) An isomer mixture containing the compound described in (8) and the compound described in (9).

(11) A glycero-compound represented by the following general formula (8):

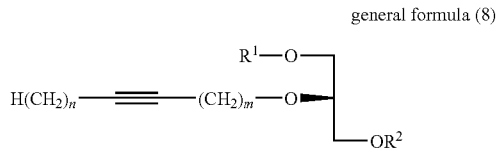

general formula (8)

wherein n, m, $R^1$ and $R^2$ are as defined in the general formula (4).

(12) A glycero-compound having a triple bond represented by the following general formula (9):

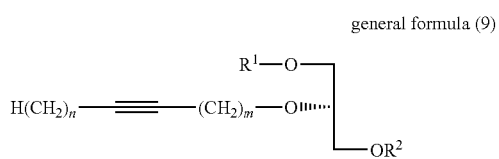

general formula (9)

wherein n, m, $R^1$ and $R^2$ are as defined in the general formula (4).

(13) An isomer mixture containing the compound described in (11) and the compound described in (12).

(14) A membrane forming material containing the compound or the isomer mixture described in any one of (1) to (13).

According to the present invention, when a fatty alcohol derivative having one triple bond and a chiral glycerol derivative compound are used, the effect capable of selectively producing a chiral compound group can be obtained. Furthermore, the glycero-compound and a membrane forming material containing the same can be produced in high purity within a short time and is not converted into a solid or its solid dispersion within a wide temperature range, and also can be used as a membrane material for forming a vesicle membrane due to its high intermolecular cohesive force.

According to the present invention, when a fatty alcohol derivative having one triple bond and a chiral glycerol derivative compound are used, an effect is obtained that a group of chiral compounds can be selectively produced. These glycerol compounds and membrane forming materials including these compounds can be produced in a high purity state and within a short period of time, and these compounds are hard to be converted into a solid or into a dispersion within a wide temperature range, and also can be used as a membrane material for forming a vesicle membrane due to its high intermolecular cohesive force, and to provide a membrane forming material containing the same.

DETAILED DESCRIPTION OF THE INVENTION

Structural formulas of the novel glycero-compounds having a triple bond according to the present invention are represented by the following general formulas (1) to (9).

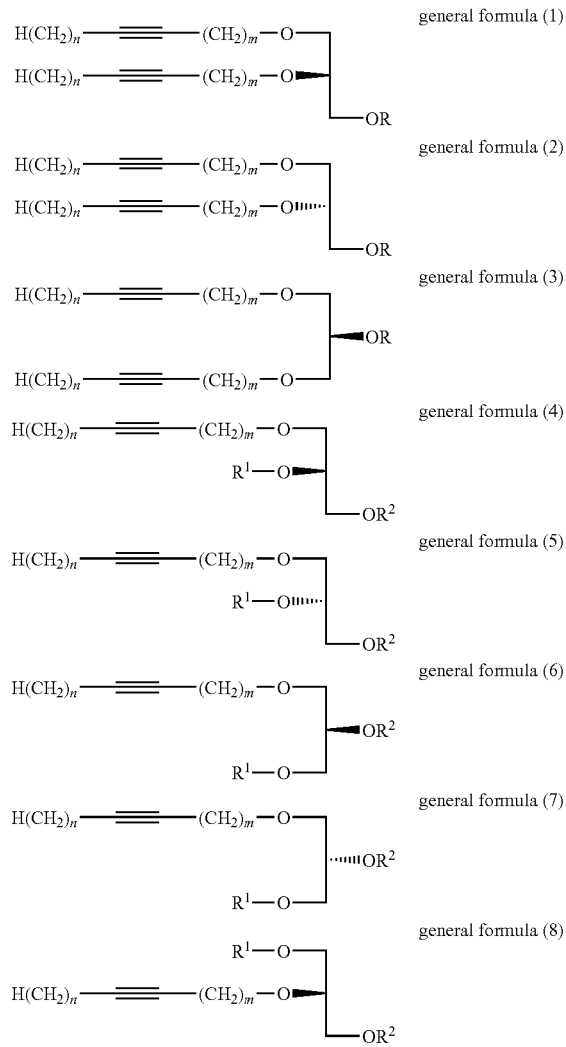

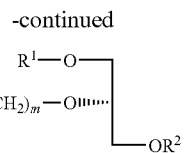

Substituents of the glycero-compounds having a triple bond represented by the general formulas (1) to (9) will now be described hereinafter in detail and compounds will be described.

R and $R^2$ represent a hydrogen atom, a metal atom, or an organic group which may be linked through a phosphoric acid group, and $R^1$ represents a hydrogen atom, an alkyl group, a cyclic alkyl group, an aryl group, or an aralkyl group.

Examples of the metal atom include atoms of alkali metals such as lithium, sodium, potassium, rubidium, and cesium; alkali earth metals such as beryllium, magnesium, calcium, strontium, and barium; and metals such as boron, aluminum, titanium, tin, and iron.

The organic group is selected from the group consisting of (1) alkyl group, (2) cyclic alkyl group, (3) aryl group, and (4) aralkyl group.

These groups will now be described in detail.

(1) An alkyl group is as described below.

The alkyl group is a group selected from among linear or branched alkyl groups. The number of carbon atom of the alkyl group is usually from 1 to 100, preferably from 1 to 72, and more preferably from 1 to 32. Practical examples thereof include methyl group, ethyl group, n-propyl group, isopropyl group, n-butyl group, isobutyl group, sec-butyl group, t-butyl group, n-pentyl group, isopentyl group, 2-methylbutyl group, 1-methylbutyl group, n-hexyl group, isohexyl group, 3-methylpentyl group, 2-methylpentyl group, 1-methylpentyl group, heptyl group, octyl group, isooctyl group, 2-ethylhexyl group, nonyl group, decyl group, undecyl group, dodecyl group, tetradecyl group, hexadecyl group, octadecyl group, eicosyl group, and phytanyl group.

(2) Examples of the cyclic alkyl group include cyclopentyl group, cyclohexyl group, adamantyl group, and cholesteryl group.

(3) Examples of the aryl group include phenyl group and naphthalene group.

(4) Examples of the aralkyl group include benzyl group and phenethyl group.

The alkyl group, the cyclic alkyl group, the aryl group or the aralkyl group may have any substituent as long as it is a group which is not involved in the production reaction when the compound of the present invention is produced. Examples of the substituent include substituted or unsubstituted aryl group, carbonyl group, alkoxy group, alkoxycarbonyl group, acyl group, acyloxy group, alkyl or arylsulfonyl group, nitro group, and halogen atom. It may be linked through oxygen atom, nitrogen atom or sulfur atom (polyethylene glycol, etc.).

Examples of the halogen atom S include fluorine atom, chlorine atom, bromine atom, and iodine atom. The halogen atom may be in the state with which an organic group is substituted.

R in the above general formula includes the above-described groups (1) to (4). In addition, a group selected from among (5) saccharides, (6) amines and (7) amino acids can be used. Also these organic groups may be linked through a phosphoric acid group.

The organic group will now be described with respect to the case of the group other than the groups (1) to (4).

(5) Saccharides are not specifically limited and are usually monosaccharides and oligosaccharides. Examples of monosaccharides include pentose, hexose, deoxyhexose, heptose, amino sugar, and sulfur-containing sugar, and practical examples thereof include arabinose, ribose, xylose, glucose, galactose, mannose, fructose, rhamnose, fucose, digitoxose, cymarose, oleandrose, digitalose, apiose, hamamelose, streptose, sedoheptulose, coriose, glucosamine, galactosamine, 2-deoxy-2-methylaminoglucose, sulfoquinovose, and galactosyl sulfate ester. Examples of oligosaccharides include non-reducing oligosaccharide and reducing origosaccharide, and specific examples thereof include sucrose, trehalose, gentianose, raffinose, lactose, cellobiose, maltose, and gentiobiose.

(6) Elements contained usually in amines are composed of 1 to 50 carbon atoms, 0 to 20 oxygen atoms, 1 to 30 nitrogen atoms, and 0 to 5 sulfur atoms, preferably 1 to 35 carbon atoms, 0 to 5 oxygen atoms, 1 to 15 nitrogen atoms and 0 to 3 sulfur atoms, and more preferably 2 to 20 carbon atoms, 0 to 3 oxygen atoms, 2 to 10 nitrogen atoms and 0 to 1 sulfur atoms.

Specific examples amino acids include glycine, alanine, valine, leucine, isoleucine, serine, threonine, aspartic acid, glutamic acid, asparagine, glutamine, lysine, ornithine, arginine, histidine, hydroxylysine, cysteine, cysteine, methionine, phenylalanine, tyrosine, triptophan, proline, 4-hydroxyproline, tricholomic acid, ibotenic acid, canavanine, kainic acid, domoic acid, 1-aminocyclopropanecarboxylic acid, 2-(methylenecyclopropyl)glycine, hypoglycin A, 3-cyanoalanine, mugineic acid, mimosine, levodopa, β-hydroxy-γ-methylflutamic acid, 5-hydroxytriptophan, pantothenic acid, laminin, and betacyanine. Amines having a sulfonic acid group such as taurine are also exemplified.

These amines may be substituted with a halogen atom, and examples of the halogen atom include fluorine, chlorine, bromine, and iodine atoms and amines may be substituted with at least one halogen atom. Also a phosphoric acid group and an amino alcohol may be linked. Examples of the amino alcohol include choline, ethanolamine, and serine.

Configurations of the compounds represented by the above general formulas (1) to (9) can be expressed according to a secondary hydroxyl group of a glycerol. That is, those in which the secondary hydroxyl group of the glycerol has an R-configuration and S-configuration are exemplified.

The compound of the present invention is obtained by optical resolution or resolution with an enzyme of those in which the 1- or 2-position of a chiral glycerol, or a glycerol or hydroxyl groups at the 1- and 2-positions are protected, or obtained by using (S)-(+)-2,2-dimethyl-1,3-dioxolane-4-methanol or (R)-(−)-2,2-dimethyl-1,3-dioxolane-4-methanol, or (R)-(+)-3-benzyloxy-1,2-propanediol or (S)-(−)-3-benzyloxy-1,2-propanediol as a starting material, preliminarily protecting a portion of hydroxyl groups, reacting with the corresponding acetylene alcohol, eliminating a protecting group and optionally introducing an organic group into free hydroxyl groups.

EXAMPLES

The present invention will now be described in detail by way of example, which is only illustrative of one embodiment of the present invention and is not intended in any way to limit the present invention thereto.

Example 1

A Flow Chart for Synthesis of a Compound 7 is Shown Below

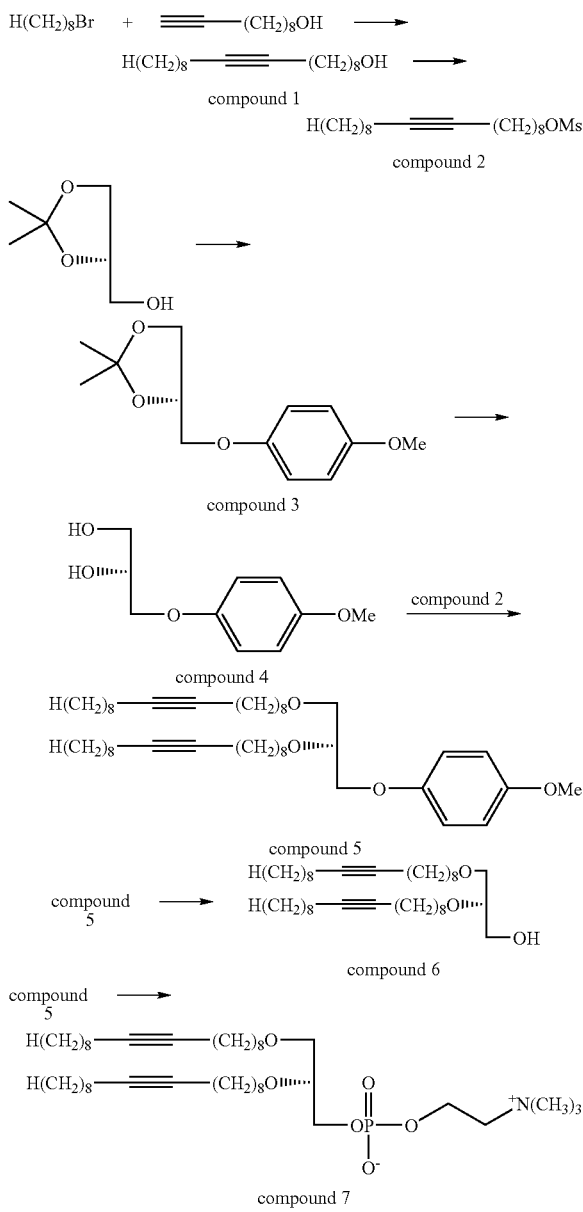

[Synthesis of Compound 1]

In an anhydrous tetrahydrofuran-anhydrous hexamethylphosphoramide mixed solution (1.2:1) of 9-decyn-1-ol (1.2 equivalents) cooled to −40° C., an n-hexane solution of n-butyllithium (1.60 mmol/ml, 2.4 equivalents) was slowly added, followed by stirring at the same temperature for 30 minutes and further stirring at 0° C. for 30 minutes. After cooling to −20° C., a hexamethylphosphoramide solution of 1-bromooctane (1 equivalent) was slowly added. After stirring at the same temperature for 10 minutes, the temperature was increased to room temperature. Stirring was conducted at the same temperature for 18 hours. Under ice cooling (at 4° C.), an aqueous 10% hydrochloric acid solution was added, followed by washing in turn with an aqueous saturated sodium hydrogen carbonate solution and saturated brine and further drying over anhydrous magnesium sulfate. After filtration, the solvent was distilled off under reduced pressure. The residue was separated by silica gel column chromatography, developing with ethyl acetate: n-hexane=3:7, to give a compound 1 in a 60-80% yield.

[Synthesis of Compound 2]

Under ice cooling (at 4° C.), methanesulfonyl chloride (1.5 equivalents) and triethylamine (2 equivalents) were added in turn to a dichloromethane solution of the compound 1 (1 equivalent), followed by stirring at the same temperature for 3 hours. An aqueous 10% hydrochloric acid solution was added, followed by extraction with dichloromethane, washing with saturated brine and further drying over anhydrous magnesium sulfate. After filtration, the solvent was distilled off under reduced pressure. The residue was separated by silica gel column chromatography, developing with ethyl acetate: n-hexane=3:7 to give a compound 2 in a 79-99% yield.

[Synthesis of Compound 3]

To a dimethyl sulfoxide solution of potassium hydroxide, (S)-(+)-2,2-dimethyl-1,3-dioxolane-4-methanol and p-methoxybenzylbromide were added, followed by stirring at room temperature for 4 hours. Under ice cooling (at 4°), an aqueous 10% hydrochloric acid solution was added, followed by extraction with ethyl acetate, washing in turn with an aqueous saturated sodium hydrogen carbonate solution and saturated brine and further drying over anhydrous magnesium sulfate. After filtration, the solvent was distilled off under reduced pressure. The residue was separated by silica gel column chromatography, developing with ethyl acetate: n-hexane=3:7, to give a compound 3 in a 83-99% yield.

[Synthesis of Compound 4]

To a methanol solution of the compound 3, a catalytic amount of p-toluenesulfonic acid monohydrate was added, followed by stirring at room temperature overnight. The solvent was distilled off under reduced pressure and an aqueous saturated sodium hydrogen carbonate solution was added, followed by extraction with chloroform, washing with saturated brine and further drying over anhydrous magnesium sulfate. After filtration, the solvent was distilled off under reduced pressure. The residue was separated by silica gel column chromatography, developing with ethyl acetate: n-hexane=1:1 to 75:25, to give a compound 4 in a 73-93% yield.

[Synthesis of Compound 5]

Under ice cooling (at 4° C.), an anhydrous N,N-dimethyl formamide solution of the compound 4 (1 equivalent) was slowly added to an anhydrous N,N-dimethyl formamide suspension of sodium hydride (60%, 2.5 equivalents), followed by stirring at the same temperature for 30 minutes. Subsequently, an anhydrous N,N-dimethyl formamide solution of the compound 2 was slowly added and a catalytic amount of tetrabutylammonium iodide was finally added, followed by stirring at room temperature overnight. Under ice cooling (at 4° C.), an aqueous 10% hydrochloric acid solution was added, followed by extraction with ether, washing in turn with an aqueous saturated sodium hydrogen carbonate solution and saturated brine and further drying over anhydrous magnesium sulfate. After filtration, the solvent was distilled off under reduced pressure. The residue was separated by silica gel column chromatography, developing with ethyl acetate: n-hexane=3:7, to give a compound 5 in a 65-85% yield.

[Synthesis of Compound 6]

Under ice cooling (at 4° C.), dichlorodicyanoquinone (1.5 equivalents) was added to a mixed solution (10:1) of dichloromethane of the compound 5 (1 equivalent) and phosphate buffer (pH7), followed by stirring at room temperature for 3 hours. Under ice cooling (at 4° C.), an aqueous saturated sodium hydrogen carbonate solution was added, followed by extraction with dichloromethane, washing with saturated brine and further drying over anhydrous magnesium sulfate. After filtration, the solvent was distilled off under reduced pressure. The residue was separated by silica gel column chromatography (eluting with ethyl acetate:n-hexane=3:7) to give a compound 6 in a 70-90% yield.

The structure of the compound 6 was determined by $^1$H-NMR.

$^1$H-NMR (TMS, CDCl$_3$) d: 3.75-3.40 (m, 9H), 2.18 (t, J=6.1 Hz, 1H), 2.14 (t, J=7.2 Hz, 8H), 1.60-1.53 (m, 4H), 1.50-1.44 (m, 8H), 1.39-1.27 (m, 36H), 0.88 (t, J=7.0 Hz, 6H).

[Synthesis of Compound 7]

Triethylamine and a phosphorus reagent were added in turn to a benzene solution of the compound 6 (1 equivalent), followed by stirring at room temperature overnight. The solvent was distilled off under reduced pressure and distilled water was added, followed by stirring at room temperature overnight. After extracting with chloroform, the solvent was distilled off under reduced pressure. A mixed solution of isopropanol:acetonitrile:chloroform (5:5:3) and an aqueous trimethylamine solution (30 to 40%) were added in turn, followed by heating at 60° C. overnight. The solvent was distilled off under reduced pressure and the residue was separated by silica gel column chromatography (eluting with chloroform:methanol:water=65:35:4) to give a compound 7 in a 75-95% yield.

The structure of the compound 7 was determined by $^1$H-NMR.

$^1$H-NMR (TMS, CDCl$_3$) d: 4.26 (bs, 2H), 3.90 (t, J=6.1 Hz, 2H), 3.62-3.53 (m, 6H), 3.49-3.41 (m, 3H), 3.24 (s, 9H), 1.53 (bs, 4H), 1.25 (bs, 60H), 0.88 (t, J=7.0 Hz, 6H).

Example 2

Formation of Membrane of Compound 7

The pasty compound 7 was interposed between a slide glass and a cover glass and then visually observed at room temperature (25° C.) under a polarizing microscope. When distilled water was added to these samples, a lamellar liquid crystal (hydrophobic group chain is in a liquid state) was formed and also a myelin figure having a tubular giant structure comprising multi lamellar structures was formed. The compound 7 was not solidified even when cooled to 0° C.

When slight external force such as ultrasonic wave is applied, a vesicle membrane having an inner water phase was produced. For comparison, a saturated linear glycerophospholipid (1,2-distearoylglycero-3-phosphocholine) having the same chain length of the hydrophobic group chain was observed under a polarization microscope. As a result, even if distilled water was added, water did not penetrate at room temperature and a crystal was maintained and easily workable lamellar liquid crystal was not formed. That is, in the case of the compound 7, a lamellar liquid crystal can be easily formed at low temperature and a lamellar structure is not collapsed by dilution with water and also a vesicle membrane can be stably formed, as compared with a saturated linear glycero-lipid having the same chain length of the hydrophobic group.

Example 3

Membrane Structure of Compound 7

An excess amount of water was added to the compound 7 and X-ray diffraction measurement was conducted at room temperature (25° C.). As a result, a fluid liquid crystal membrane having a thickness of 3.4 to 3.7 nm was formed and an molecular occupied area of a compound A in the membrane was large such as about 0.7 nm$^2$/molec and exhibited a liquid-expanded behavior.

For comparison, the measurement was conducted in the same manner, using 1,2-distearoylglycero-3-phosphocholine. As a result, a 4.7 nm thick membrane in a crystal form was formed and a molecular occupied area of it in the membrane was large such as about 0.4 nm$^2$/molec (closely packed). In the case of the compound 7, a lamellar liquid crystal can be easily formed at low temperature, as compared with a saturated linear glycero-lipid having the same chain length of the hydrophobic group.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A glycero-compound having a triple bond represented by the following general formula (1):

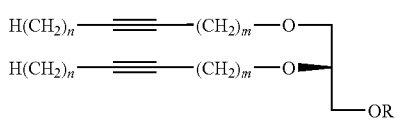

general formula (1)

wherein n and m each represents a number of 1 to 17 and the total (n+m) is a number of 4 to 18, n and m may be the same or different, and R represents a phosphoric acid group, or an organic group which is linked through a phosphoric acid group.

2. A glycero-compound having a triple bond represented by the following general formula (2):

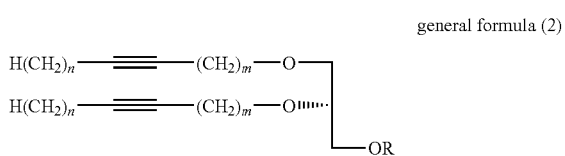

general formula (2)

wherein n and m each represents a number of 1 to 17 and the total (n+m) is a number of 4 to 18, n and m may be the same or different, and R represents a phosphoric acid group, or an organic group which is linked through a phosphoric acid group.

3. An isomer mixture containing a glycero-compound having a triple bond represented by the following general formula (1):

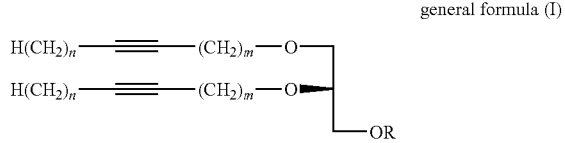

general formula (I)

wherein n and m each represents a number of 1 to 17 and the total (n+m) is a number of 4 to 18, n and m may be the same or different, and R a phosphoric acid group, or an organic group which is linked through a phosphoric acid group and the compound according to claim 2.

4. A membrane forming material containing the compound according to claim 1.

5. A membrane forming material containing the compound or the isomer mixture according to claim 3.

6. A membrane forming material containing the compound according to claim 2.

* * * * *